(12) United States Patent
Gramnas

(10) Patent No.: US 6,235,062 B1
(45) Date of Patent: *May 22, 2001

(54) FASTENING DEVICE FOR PROSTHESIS

(76) Inventor: Finn Gramnas, Brantalid 18, S-511 56 Kinna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/547,513

(22) Filed: Apr. 12, 2000

Related U.S. Application Data

(63) Continuation of application No. 09/255,665, filed on Feb. 23, 1999, now Pat. No. 6,093,210, which is a continuation of application No. 08/918,324, filed on Aug. 26, 1997, now Pat. No. 5,928,290, which is a continuation of application No. 08/705,837, filed on Aug. 30, 1996, now abandoned, which is a continuation of application No. 08/232,108, filed on Sep. 6, 1994, now abandoned.

(51) Int. Cl.[7] .................................................. A61F 2/60
(52) U.S. Cl. ......................... 623/33; 292/306; 403/325
(58) Field of Search ........................ 623/33, 38; 292/306; 403/325

(56) References Cited

U.S. PATENT DOCUMENTS

| | | |
|---|---|---|
| 991,241 | 5/1911 | Rae . |
| 1,674,081 | 6/1928 | Adams . |
| 1,854,386 | 4/1932 | Werth . |
| 2,169,875 | 8/1939 | Fanning ................................ 292/306 |
| 3,244,444 | 4/1966 | Bisbing ................................ 292/306 |
| 3,374,011 | 3/1968 | Schipper .............................. 280/478 |
| 3,468,579 | 9/1969 | Tabor ................................... 292/306 |
| 3,588,023 | 6/1971 | Cohen ................................... 248/410 |
| 5,116,382 | 5/1992 | Steinkamp et al. .................... 623/38 |
| 5,547,308 | 8/1996 | Wright ................................. 403/325 |
| 6,106,559 * | 8/2000 | Meyer .................................. 623/33 |

FOREIGN PATENT DOCUMENTS 1142527    3/1960   (DE) .

* cited by examiner

Primary Examiner—Bruce Snow
(74) Attorney, Agent, or Firm—Gardner, Carton & Douglas

(57) ABSTRACT

A fastening device for a prosthesis, the fastening device having a cylindrical channel and an inclined washer designed to accept insertion of a cylindrical inset, such as a tube, bar or peg, with minimal resistance and yet substantially prevent withdrawal of the cylindrical insert from the fastening device unless a release mechanism is operated to permit withdrawal. The device permits rotation of the cylindrical inset with respect to the fastening device while still securely fastening the cylindrical insert within the fastening device, so as to prevent unlocking of the device and separation of the cylindrical insert.

3 Claims, 1 Drawing Sheet

FASTENING DEVICE FOR PROSTHESIS

CROSS-REFERENCES TO RELATED APPLICATION

This application is a continuation of application Ser. No. 09/255,665 filed Feb. 23, 1999, now U.S. Pat. No. 6,093,210, which is a continuation of application Ser. No. 08/918,324, filed Aug. 26, 1997, now U.S. Pat. No. 5,928,290, which is a continuation of application Ser. No. 08/705,837, filed Aug. 30, 1996, now abandoned, which is a continuation of application Ser. No. 08/232,108, filed 1994, now abandoned.

BACKGROUND OF THE INVENTION

The present invention relates to a fastening device and further relates to a fastening device for a prosthesis, the fastening device having a cylindrical channel and inclined washer designed to accept insertion of a cylindrical insert, such as a tube, bar or peg, with minimal resistance and yet substantially prevent withdrawal of the cylindrical insert from the fastening device unless a release mechanism is operated to permit withdrawal. In addition, the present invention relates to a fastening device which permits rotation of the cylindrical insert with respect to the fastening device while still securely fastening the cylindrical insert within the fastening device, so as to prevent unlocking of the device and separation of the cylindrical insert.

The present invention has been developed especially in order to be used as a fastening device for prostheses, for example artificial legs, to a prosthesis sleeve which is attached to an amputated leg, but it may also be used in many other connections where a device with the corresponding quality and function is desired. The problems, which are solved by the invention connected with the fastening device for prostheses, are to obtain a safe fastening and simple detaching without tools. Moreover, the fastening device has to allow a certain turning movement and lock steplessly without backlash against moving apart when loaded and with compression between prosthesis and prosthesis sleeve. These and other problems are solved with a fastening device according to the invention, comprising a house with an inclined washer, which can be turned and is kept inclined by a spring in a way which appears clearly from the special part of the description, and a cylindrical part, for instance in the form of a peg on the part which the part with the fastening device is to be connected to.

It is known to use inclined, elastic or spring loaded thin metal elements with holes slightly bigger than the tube or rod which is locked in one direction by the metal element. These are used for example as jacks, door closers, etc. In these cases the metal element and the tube or rod are often mutually guided in such a way that no relative turning can be done. Because this would generally mean that the locking action of the inclined metal element will come to an end. Therefore, before the come about of the present invention it has not been possible to use this simple locking principle in those cases where a secure locking has been neccessary also in combination with a possibility of relative turning and detaching of the metal element with its locking function from the tube or rod.

BRIEF DESCRIPTION OF THE DRAWINGS

In the following the invention will be closer described referring to the enclosed drawings, in which.

DETAILED DESCRIPTION OF THE INVENTION

Figure 1:
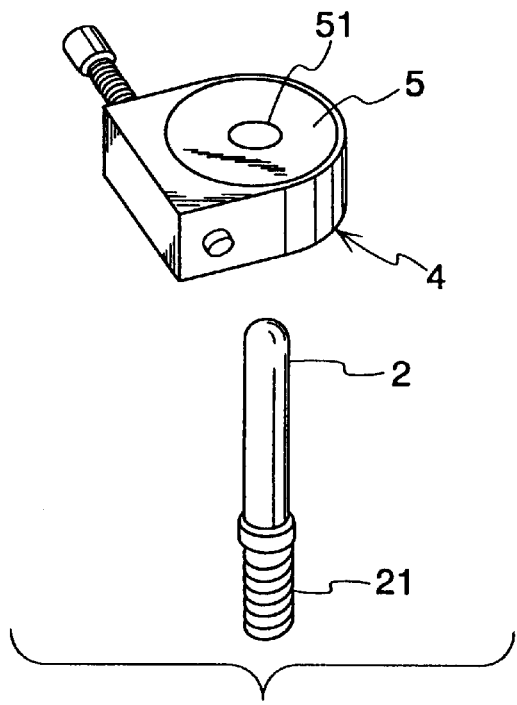
FIG. 1 shows in perspective a fastening device according to the invention and a peg not combined.
Figure 3:
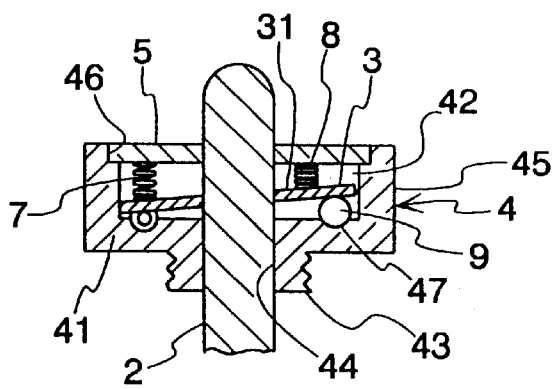
FIG. 3 shows section A—A from the side in FIG. 2.
Figure 4:
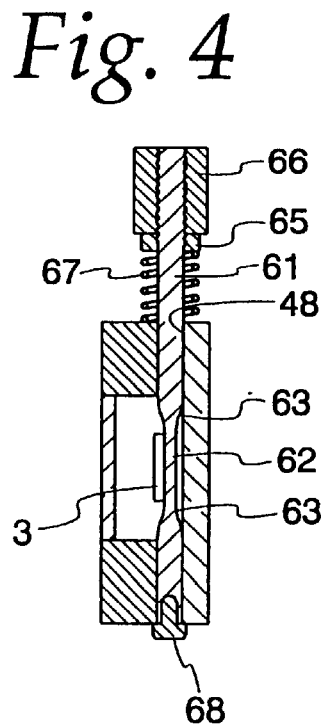
FIG. 4 shows section B—B in FIG. 2.
Figure 2:
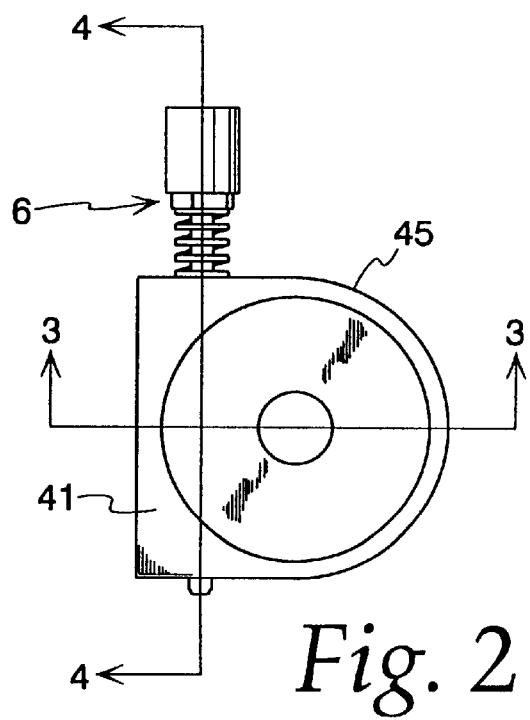
FIG. 2 shows the fastening device with the peg brought together in a view from above.

As appears from the drawings, an embodiment of a fastening device 1 according to the invention consists of a hollow house 4 with a lid 5, the cavity containing a washer 3, a first spring 7, a second spring 8 and a ball 9. A peg 2, which is put through a central hole 44 in the house and through a central aperture or hole 31 in the washer and possibly further on through a central hole 51 in the lid is secured from being moved apart by the washer 3, seated on the ball 9 and the central aperture 31 of which is securing to the peg 2 by the force from the springs 7 and 8. The fastening device 1 is also equipped with a releasing device 6, bringing the washer against the force of springs 7 and 8 in order to release the peg 2 from engagement in the hole 31 of the washer 3.

In order to obtain a secure function of the device certain conditions must be fulfilled. The ball 9 should be in a position mainly diametrically opposed to the outer, first spring 7, which secures the locking action of the washer. The inner, second spring 8 serves to keep the washer 3 in contact with the ball 9 as the peg is inserted so that no backlash will arise in the locking function caused by that the washer is moved from the ball towards the lid when the peg is inserted. In order to fulfil thin function the second spring 8 should be situated near the ball, preferrably between the ball and the hole for the peg, and its spring force should be substantially bigger than that of the first spring 7. The springs 7 and 8 are coil springs kept in place by being countersunk in and/or fastened to the lid. The springs 7 and 8 may also be made of conical coil springs in order to reduce the height of the fastening device. Alternatively, one or both springs may be made as plate springs with tongues springing out from a spring bottom which bears on the lid 5. It is also possible to replace the springs 7 and 8 with one single coil spring with a suitable dimensioning and placement, for instance around the hole 31.

Moreover, the washer 3 must be so designed, that its central hole 31 has a diameter slightly bigger than that of the peg 2. With 8 mm diameter of the peg 2 and a thickness of 1.5 mm of the washer 3 it is suitable that the diameter of the hole is up to 0.1 mm bigger, preferrably 0.04–0.05 mm bigger than that of the peg 2.

It is the combination of a ball 9, against which the washer easily can slide or roll, and the mainly diametrically contacting spring 7, against which the washer also can slide with a low friction, that makes the washer lock securely also if the peg with the washer are turned in relation to the fastening device. This is, of course, possible to achieve otherwise than with the ball 9. This can for instance be substituted by every other discrete contact point which can give the same quality with or without lubrication, such as a sliding surface, a roll or the like. The contact points of the springs towards the washer may be made of a ball, a bearing surface or another suitable design as well. It is also possible as an alternative within the scope of this invention, even though this gives a more complicated construction, to surround the washer, its contact point and the springs with a bearing in the house so they can rotate with the peg.

The house 4 consists of a main part 41 with a cylindrical cavity or recess 42, with a central hole 44, also leading through a threaded part 43 arranged on the bottom side of the main part. The wall 45 of the main part extends in the shape of half a circle around one half of the recess 42 but forms around the other half a rectangular profile, through which a channel 48 for the releasing device 6 runs. The channel 48 is arranged with its center line at the bottom of the cylindrical recess 42 in such a way that all of the channel for one part is situated within the circumference of the recess 42. Around the upper part of the recess 42 an enlargement 46 is made so that the lid 5 can be mounted therein, preferably with a snap action. At the bottom of the recess is also arranged a countersink 47 for the ball 9.

The releasing device 6 consists of a shaft 61 ground with at least one conical part 63 to a narrow part 62 of even thickness, normally situated opposite the middle of the washer 3. One end of the shaft 61 is threaded and equipped with a nut 65 and a sleeve 66 and a coil spring 67 is arranged between the nut 65 and the main part 41 of the house. The shaft 61 is retained against action of the spring 67 by a screw 68 arranged at the end of the shaft with its head normally bearing upon the house 4. The function of the releasing device 6 is such that its conical part 63 lifts the washer 3 when the shaft 61 is moved axially by pressing on the sleeve 66, by which the central hole 31 of the washer releases its hold of the peg 2. The end of the peg is equipped with a thread 21 in order to be attached to for instance a prosthesis sleeve, and the house 4 with its threaded part 43 can be attached to a prosthesis, or vice versa.

The invention has now been described in detail with reference to a preferred embodiment. However, several modifications are possible within the scope of the invention, which shall only be restricted by the wording of the following claims. Thus, when appropriate, the peg can be substituted by a long rod or a tube and the releasing device can be substituted by every other suitable mechanism influencing the washer from its inclined position towards a position perpendicular to the peg. Of course, the design of the house and the lid can also be altered.

What is claimed is:

1. A device for fastening a prosthesis on to a prosthesis sleeve, wherein the prosthesis sleeve is equipped with a cylindrical peg having a smooth end, the device comprising:

a housing;

a cylindrical channel positioned within the housing adapted to receive the peg;

a recess positioned within the housing;

at least one spring positioned within the recess;

an inclined washed having a central aperture, the washer being received within the recess and is kept inclined by spring force by the spring in such a way that the central aperture, which is slightly greater than the diameter of the peg, prevents movements of the fastening device axially along the peg even if the fastening device is rotated about the peg, a first contact point between the washer and a ball against which the washer is borne by the spring to ensure that the washer is kept in contact with the first contact point, wherein the first contact point preventing axial movement of the peg while allowing the housing to be rotated about the peg, a second contact between the spring and the washer, wherein the second contact point being a low friction surface, and a release device acting on the washer against the spring forces so that the force on the washer decreases.

2. The device according to claim 1 wherein the release device comprises a shaft with a conical part arranged so that the conical part raises the washer when the shaft is displaced axially.

3. The device of claim 1 wherein the first contact point is a low friction surface.

* * * * *